United States Patent [19]
Tucker et al.

[11] 3,955,436
[45] May 11, 1976

[54] LIQUID SAMPLING AND CONTAINER HANDLING APPARATUS

[75] Inventors: Howard E. Tucker; James A. Corll, both of Los Alamos, N. Mex.; Walter R. Hogg, Miami Lakes, Fla.

[73] Assignee: Particle Technology, Inc., Los Alamos, N. Mex.

[22] Filed: Mar. 10, 1975

[21] Appl. No.: 557,066

[52] U.S. Cl. ............................ 73/421 R; 73/423 A
[51] Int. Cl.[2] .......................................... G01N 1/10
[58] Field of Search ................... 73/421 B, 423 A; 356/246; 23/253 R

[56] References Cited
UNITED STATES PATENTS

| | | | |
|---|---|---|---|
| 2,693,705 | 11/1954 | Casler et al. | 73/421 B |
| 3,826,621 | 7/1974 | Johnson, Jr. et al. | 73/423 A |

*Primary Examiner*—S. Clement Swisher
*Attorney, Agent, or Firm*—Silverman & Cass, Ltd.

[57] ABSTRACT

Liquid sampling apparatus including a sampling head incorporating a floating pressure seal effected by a positive pressure introduced into an open top sample container in which the sampling head is telescopically introduced. The liquid sampling apparatus includes a compartment having at least an entrance, a cover slidable within said compartment and the sliding cover carrying the sampling head. The sliding cover has a depending shield capable of closing off the entrance to the compartment when the assembly head is therein introduced.

The floating pressure seal is defined by a mounting ring seated in a suitable passageway formed in the cover. The mounting ring has a central aperture and a plunger is slidable within said aperture, one end of the plunger being threaded and having an adjusting ring threadably engaged thereupon for limiting the extent of free movement of the plunger relative to the mounting ring. The other end of the plunger has an enlarged head or piston. The mounting ring and the plunger have facing tapered surfaces defining a groove and an expandable O-ring is seated therewithin. A pair of parallel conduits are provided passing through the plunger and piston. One of the conduits is coupled to a source of positive pressure and the other leads to a destination for the withdrawn sample. The open top sample container is coupled to the sample head and both are introduced into the compartment. A positive pressure is introduced to the sample container which first forces the piston upwards to expand the O-ring establishing a pressure-type seal between it and the inner wall of the vessel. The positive pressure is increased to force liquid from the container.

26 Claims, 6 Drawing Figures

LIQUID SAMPLING AND CONTAINER HANDLING APPARATUS

BACKGROUND OF THE INVENTION

1. Field of the Invention

This invention relates generally to liquid sampling apparatus and more particularly provides a quick change sample cup handling apparatus for utilization with liquid sampling apparatus wherein plural sample cups are introduced successively to a pressure-type sampling head for withdrawing liquid therefrom with safety and efficiency.

Many analytical procedures, particularly procedures involving automated methods and means, require an original sample introduction to the analytical system. Among apparatus for effecting such introduction are those generally involving the withdrawal, by probe means or the like, of a given quantity of liquid which is contained in an open top sample container. In many instances, the container is brought to the probe or other sampling means by manual manipulation and held therein by the operator until sampling is completed. In order to increase efficiency, minimize handling and maximize the speed in which plural sample containers can be handled, the provision of apparatus capable of handling such sampling containers one after the other with safety and efficiency is desirable. Often pressure systems and/or vacuum systems are utilized to effect the withdrawal of such liquid samples with pressure displacement of liquids from containers being widely used.

Considerable difficulty has been encountered in the implementation of such techniques. One problem involves the provision of an effective and rapidly made seal between the sampling head and the sampling container, which seal can be quickly and easily disengaged once the sampling has been completed. In addition to the implementation of speedy handling and the reduction in the problems encountered where manual manipulation and handling of sample vessels occur, safety also is a prime consideration. Safety consideration includes not only protection from fracture of the container and resultant spillage, but error in grasping, moving and otherwise manipulating the sample containers. At the same time, one must consider the speed of the overall operation and the rapidity by which the containers can be handled, the liquid samples therein probed, the seal effected, the liquid transferred and the sample containers withdrawn. Where automatic or semiautomatic apparatus is considered, the manipulation of sample containers often is a factor amounting to a deterrent to obtaining maximum benefit from the use of such automated or semiautomated apparatus.

The apparatus herein is intended to provide a solution to the problems enumerated above.

BRIEF SUMMARY OF THE INVENTION

A sampling apparatus enabling liquid to be withdrawn from an open topped vessel by pressure introduced therein while the vessel is engaged upon a sampling head having a pair of conduits and a floating pressure seal, the sampling head being carried by a wall of a compartment. The vessel is telescopically engaged frictionally with the sampling head and while so engaged the head and the vessel are disposed in the compartments. A positive pressure is applied causing the seal to be effected and thereafter further pressure is introduced to drive the fluid content of the vessel through one of said conduits which is introduced into the liquid within the vessel. Pressure relief after sampling functions to release the seal from its maximum effectiveness. The container then is withdrawn to the exterior of the compartment. The container can easily be disengaged from the sampling head and a new container substituted.

DESCRIPTION OF THE PREFERRED EMBODIMENTS

The sampling apparatus of the invention is intended to provide means whereby the operator can introduce a container carrying a liquid sample to a sampling head, withdraw the desired quantity of liquid sample therefrom and disengage the sample container from the sampling head and rapidly introduce a further or other container to the sampling head. Sampling is conducted within an enclosure. A compartment is defined including a platform, an entrance and a sampling head carried by one of the compartment defining structural components, the sampling head capable of being positioned above the platform in communication with the compartment. The sample container has an open top and is brought into engagement with the sampling head. Both are introduced into the compartment. The sampling head is provided with a floating pressure seal capable of establishing a pressure seal between the container and the head when the container is seated on the platform within the compartment. A positive pressure is introduced into the container first to effect the pressure seal and next to effect a displacement of the liquid and transfer thereof to a destination exterior of the apparatus.

Preferably, the sampling head is carried by a plate slidably movable into and out of the compartment. The container manually is placed in frictional engagement with the head and the sliding plate is manipulated to position the head and container interior of the compartment. The plate has a depending wall for closing off the compartment when the head and container have been fully introduced therein. The height of the compartment is selected so as just to accommodate the engaged head and container.

The floating pressure seal is constructed to effect a pressure-type seal upon introduction of a positive pressure to the container when the sampling head is engaged frictionally, telescopically within the open top of the container and both are within the compartment. Further application of positive pressure causes the liquid carried by the container to be displaced therefrom by way of conduit means carried by the sampling head and leading to a destination.

Figure 1:
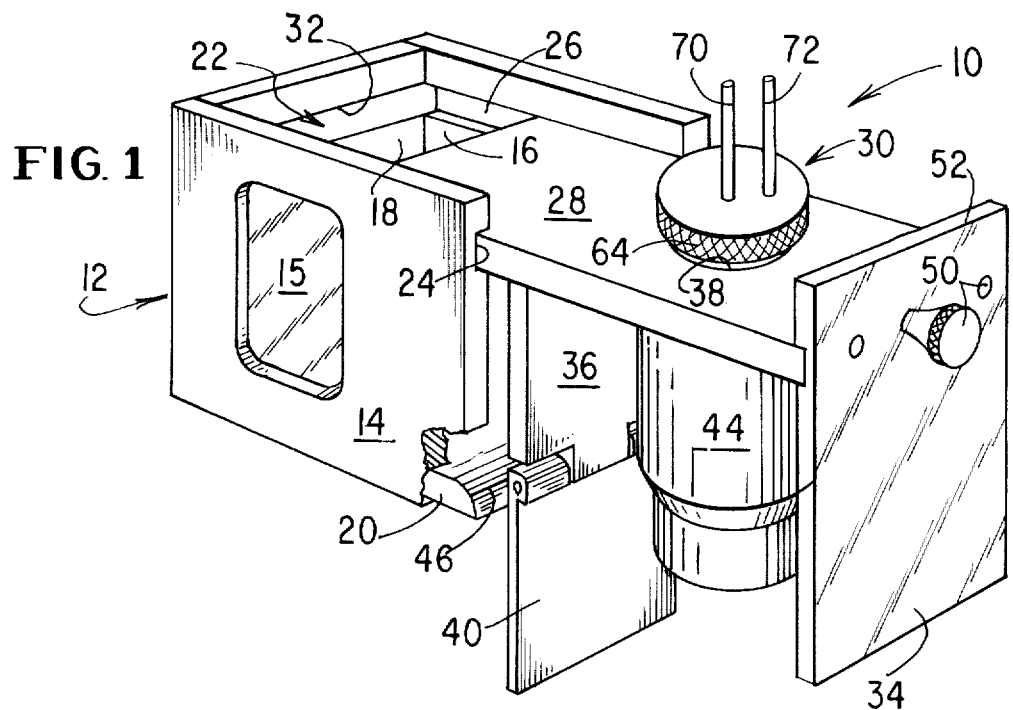
FIG. 1 is a perspective view of the sampling apparatus constructed in accordance with the invention, the same being illustrated in open condition.
Figure 2:
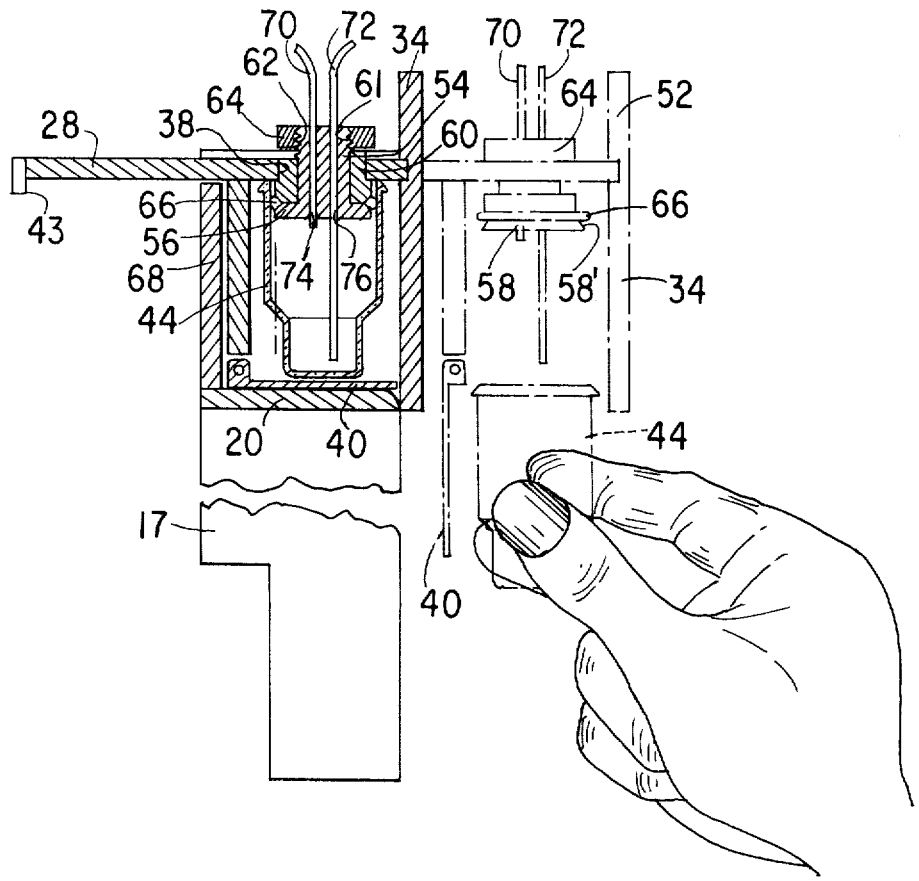
FIG. 2 is a side elevational sectional view of the sampling apparatus of FIG. 1 shown with the sample container in condition for sampling, the phantom lines representing the condition assumed during the introduction of the sample container to the sampling apparatus.
Figure 3:
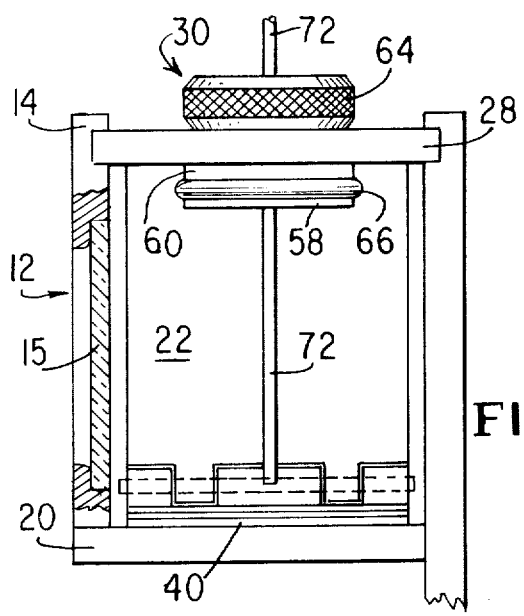
FIG. 3 is a front elevational view of the apparatus portions shown in section and without the sample container.

Referring now to the drawings, in FIG. 1, the sampling apparatus 10, according to the invention, comprises a rectangular body 12 formed by side walls 14 and 16, rear wall 18 and bottom wall 20 which define compartment 22 therein. The side walls 14 and 16 have opposite channel-defining parallel grooves 24 and 26 formed near the upper ends of the side walls coextensive therewith and aside end configuration to enable a plate member 28 to be arranged therein for slidable movement therealong. The sampling head 30 is seated upon the plate member 28 so that as the plate is moved slidably in the direction of the rear wall 18, the sampling head is carried into the compartment. The rear wall 18 has a slot 32 formed thereacross at the same level as the grooves so that the plate 28 can pass therethrough. The rear wall 18 may be shorter than the side walls in lieu of forming the slot 32.

The plate 28 carries a pair of spaced depending parallel walls 34 and 36 and a generally circular passageway 38 is formed in the plate 28 between the walls 34 and 36. Wall 34 preferably is formed of a transparent, impact resistant material such as a polycarbamate, and is of sufficient length and width to cover the entrance to the compartment when the plate has been slidably urged along the grooves 24 and 26 fully to position the sampling head within the compartment. Wall 36 is shorter than wall 34 and carries a flapper member 40 pivotably mounted thereto at the lower edge thereof, the flapper 40 being formed preferably of generally flexible material. The length of the flapper 40 is selected so that it is less than the length of the floor or bottom wall 20. The flapper 40 hangs free when the plate 28 is extended from the compartment and is caused to pivot upwards when the plate is slidably moved along the grooves 24 and 26 to place the sampling head 30 within the compartment. The plate may have stop means in the form of flange 43 at one end thereof so as to limit the extension of the plate whereby to prevent its being drawn from the grooves 24 and 26.

With one hand, the operator places the open topped container, here designated by reference character 44, frictionally engaged upon the sampling head 30 and at the same time urges the plate along the grooves so that the engaged sampling head and container are introduced into the compartment as a unit. As the sampling head and container are introduced into the compartment by sliding of the plate along the grooves 24 and 26, the flapper is caused to pivot upwards so that when the sampling head and container unit is positioned fully within the compartment, the flapper has assumed a generally horizontal disposition and is capable of being supportive of the container. The front edge 46 of the bottom wall 20 of the compartment is rounded to facilitate smooth pivoting of the flap as it enters the compartment and as well, to facilitate the withdrawal of the container once the sampling is completed.

The depending wall 34 which is secured to the front edge of the plate 28 by screws 50 or like fastening means has a portion 52 which extends above the plate 28 and functions as a pusher or handle to facilitate the movement of the plate. As stated heretofore, the material and thickness of the wall 34 is selected to be shatterproof in order to protect the operator from the effect of an explosion should the sample container shatter under the influence of the positive pressure introduced into the same during the sampling procedure. Preferably, the wall 34 is formed of transparent material so the operator can view the interior of the compartment.

The sampling head 30 which is carried by the plate 28 is seated within the circular passageway 38. The sampling head 30 includes a cylindrical body 54 having an enlarged head 56, the outer surface 58' thereof being flat and the undersurface 50 being tapered toward the body 54. The enlarged head 56 functions as a piston relative to the interior of the container. The remainder of the body 54 functions as a plunger and is threaded along the free end 61 thereof, and 61 being the opposite end relative to the enlarged head portion 56. An annular mounting collar 60 is provided and is of size and configuration enabling the same to be seated within the circular passageway 38 formed in the plate 28. The collar 60 has an axial passage 62 for receiving the body 54 for free slidable movement therethrough. The body 54 first is passed through the passageway 62 from the undersurface of the plate 28 and is secured on the opposite side of the plate 28 by adjusting nut 64 which is threadably engaged upon the threaded portion 62 of body 54. The relative disposition of the adjusting nut 64 along the body 54 determines the range for free movement of the body through the collar 60. A ring 66 of resilient, expandable material is interposed seated in the groove 66 defined between the undersurface of the collar 60 and the tapered portion 68 of the enlarged head 56. The width of groove 66 varies with the position of head 56. A pair of parallel conduits 70 and 72 are engaged through suitable axially extending bores 74 and 76 formed in the body 54. One conduit 70 extends only a small distance outward of the surface of 58 of head 56 while the other conduit 72 extends a substantial distance outward relative to conduit 70. The first conduit 70 preferably is coupled by valve means or the like to a source of positive pressure and the second conduit 72 is coupled to a predetermined location where it is desired to transfer the withdrawn liquid sample. Generally, the conduit 72 is long enough to reach interior of the container and terminate close to the bottom thereof when the container is engaged upon the sampling head 30.

In operating the liquid sampling apparatus 10, the open top container is held by the operator and frictionally engaged upon the sampling head 30 sufficiently to clear the floor 20 of the compartment 22. The plate 28 is slidably urged along grooves 24, 26 to position the sampling head 30 and the sample container engaged thereupon within the compartment 22. Of course, the flapper is pivoted to a condition supportive of the container when the same is within the compartment 22. Partway along, operator can release his grip on the container with the flapper 40 now supporting the container. Accordingly, the engaged container and sampling head is introduced fully into the compartment 22 at which time the wall 34 covers the entrance to the compartment 22. The positive pressure then is applied by way of conduit 70 to the interior of the container. The pressure exerts force upon the flat head 58 of the piston 54 (enlarged portion) to drive same upwards the distance determined by the position of the adjustment nut upon the threaded portion of body 54. The sealing ring 66 is forced to expand against the inner wall of the container thereby defining a pressure-tight seal. Additional pressure of a positive nature is introduced into the container to drive the liquid within the container into the second conduit 72 and thence to a predetermined location. Relief of the pressure enables quick release of the expanded ring from the inner wall of the container, breaking the seal. The plate then can be withdrawn along the channel means. The container is carried by the flapper 40 until it can be grasped manually by the operator and fully withdrawn from the compartment. Thereupon it is released from the sampling head. The flapper carries the container with the movement of the plate so that the container is not upset by its withdrawal from the compartment on the reverse direction movement of the plate 28.

Figure 4:
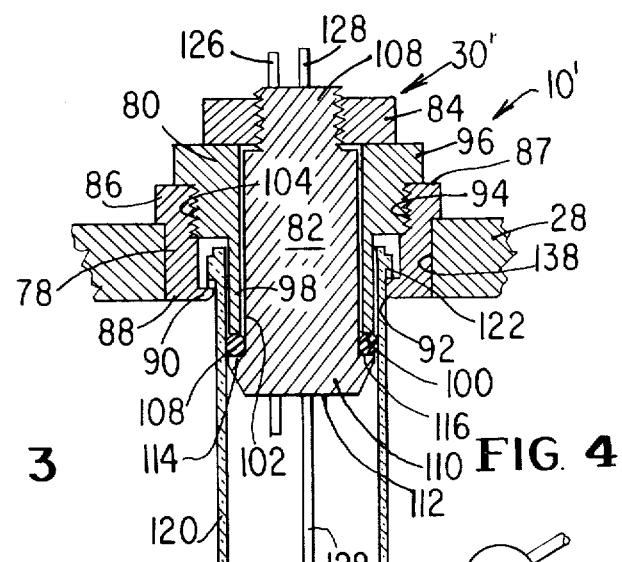
FIG. 4 is a fragmentary detail illustrating a modified embodiment of the invention.

In FIG. 4 there is illustrated a detailed representation of a modified sampling head 30' which can be utilized in place of sampling head 30. The sampling head 30' comprises a mounting collar 78, a threaded intermediate, ringlike insert 80, a generally cylindrical body 82 slidably engaged within the insert 80 and an adjustment nut 84 threadably engaged on the generally cylindrical body 82.

The mounting collar 78 has an outer diameter sufficient to enable same to be seated within the passageway 38 formed in plate 28. The collar 78 has an enlarged outer annular overhang 86 integral therewith. Overhang 86 is seated on the plate 28 adjacent the passageway 38. The opposite end 88 of collar 78 has an inwardly extending ring 90 integral therewith, the end 88 of the collar being flush with the under surface of plate 28. The inner edge 92 of end 88 is rounded to facilitate passage of the sample container therepast, as will be explained. The intermediate insert 80 has a threaded midportion 94, an upper enlarged head portion 96, and a reduced diameter portion 98 which terminates in a flat ring 100. An axial passageway 102 is provided through the insert 80. Threaded portion 104 is engaged with the threaded portion 94 of the mounting collar 78. The annular head portion 96 rests upon the end 87 of collar 78.

The cylindrical body 82 is slightly longer than the length of passageway 102 formed in the intermediate insert 80. The diameter of cylindrical body 82 is slightly less than the inner diameter of passageway 102 so as to permit free sliding movement of the body 82 through the passageway 102.

One end 108 of the body 82 is threaded and the opposite end 110 of said body 82 is provided with an enlarged head 112. The body 82 is introduced through the passageway 102 and an interiorly threaded adjustment nut 84 is threadably engaged upon end 108.

An annular groove 114 of generally rectangular cross section is defined between the flat end 100 of insert 80 and the ledge 116 defined by the enlarged head 112 of body 82. An expansible, resilient member, here O-ring 109 is seated within the groove 114.

The sample cup 120 can be provided with an annular collar 122 arranged to engage the annular ring 90. Preferably, plural notches 124 can be provided in the collar 122 to enhance the engagement. A bayonet connection thus is defined between collar 122 and ring 90. Conduits 126 and 128 pass generally axially parallel through the body 82. Conduit 128 extends further outward of the enlarged head 112, preferable to reach the bottom of the container 120.

Figure 5:
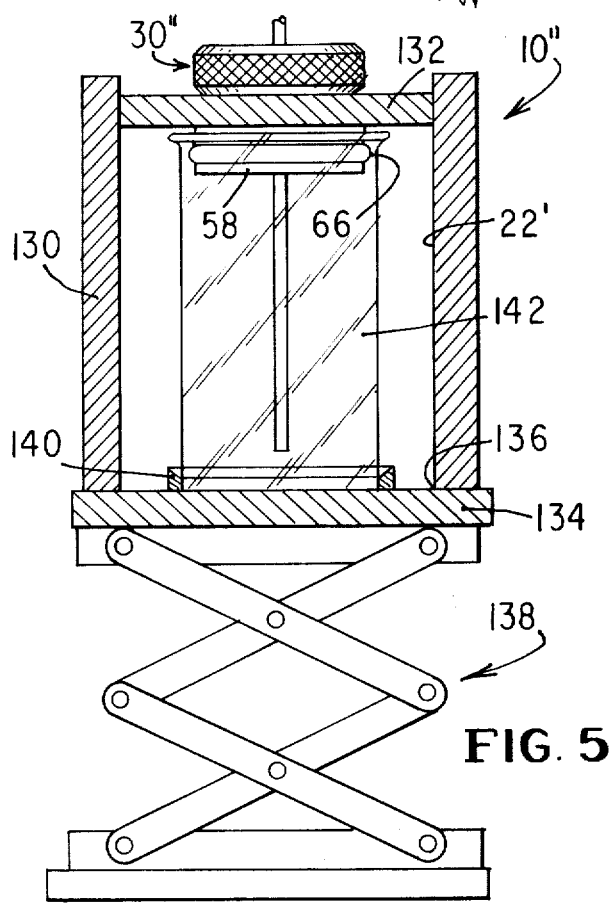
FIG. 5 is a diagrammatic representation of a further modified embodiment of the invention.

The embodiments illustrated in FIGS. 1 through 4 provide a compartment 22 having a side opening with the top of the compartment comprising the slidable plate 28. In FIG. 5 the sampling apparatus 10'' includes a compartment 22' which is defined by a hollow member 130, which can be cylindrical, a cover or top wall 132 which carries the sample head 30'' and a separate floor or platform 134 which may be raised or lowered selectively to open the bottom entrance 136. The platform is seated upon a raising and lowering mechanism 138, here represented by a jack. The platform 134 is provided with retaining means, such as raised annular ring 140 which positions a container 142 coaxially with the sampling head 30''. The cup 142 is seated within ring 140 and the floor or platform 134 is raised to a height where the sampling head 30 is telescopically engaged within the open top of cup 142. Once the sampling head is engaged within the open top of cup 142, the positive pressure may be introduced into the cup to establish the pressure-tight seal. After sampling and pressure relief, the floor 134 is lowered enabling the container to be removed.

Figure 6:
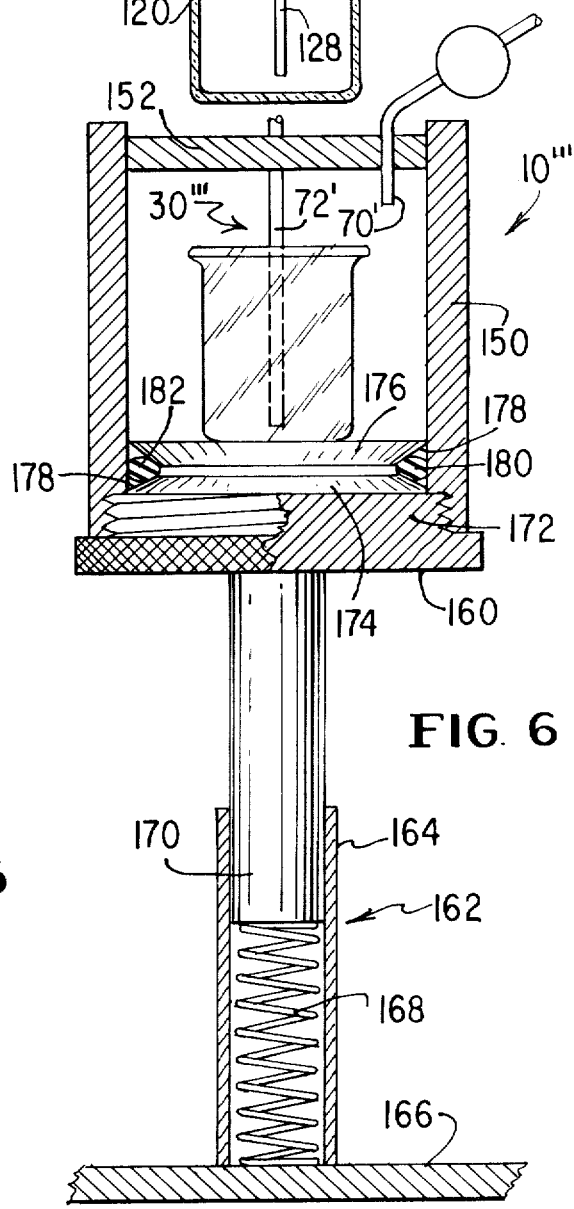
FIG. 6 is an elevational view of a further modified embodiment of the invention, portions being shown in section.

In FIG. 6, a further modified embodiment of the invention is illustrated. Here the sampling apparatus 10''' comprises a bottom opening cylindrical member 150 having a top portion 152 through which a sampling head 30''' is mounted. In this instance, the sampling head 30'' merely consists of a pair of conduits, 70' and 72', one 72' of which is arranged to extend into a sample container and the other 70' simply extends into the interior of the cylinder 150. A movable platform 160 is provided. The movable platform is seated on a stand 162. The stand 162 has an upstanding cylindrical portion 164 and a base 166. A spring 168 is seated within the interior of the upstanding portion 164. The platform is mounted upon a depending shaft 170 which is seated on the spring within the stand. The platform 160 has a threaded seat portion 172 on which a pair of annular disks 174, 176 freely rest. The annular disks 174, 176 having facing tapered surfaces 178 defining a groove 180 in which an expansible O-ring 182 is seated. The sample container is seated on the disk and a connection made between the cylinder and the threaded portion of the platform is established. Positive pressure is introduced through conduit 70' into the compartment defined interior of the cylinder 150. The head of positive pressure causes the upper disk 176 to bear against the O-ring 182 and establish a pressure-tight seal. Further admission of pressure causes the fluid interior of the container to be displaced and passed through the conduit 72' to a desired location.

A viewing window 15 can be formed in wall 14 of body 12, while wall 16 thereof can be a part of a mounting bracket, represented by reference character 17. Obviously, the effective height of the compartment is such as to just clear the engaged sampling head and container.

Where the sampling head 30'' is used, the conduit 72' should be long enough to reach at least close to the bottom of the container. Plural conduits 72' can be used, with the capability of simultaneously withdrawing plural samples, one from each of plural containers into which the conduits 72 are each introduced. With the use of sampling apparatus 10'', the configuration of the container is not critical nor is the size so long as the container is fully enclosed within the defined compartment.

What we claim is:

1. Sampling apparatus for withdrawal of liquid samples from an open top sample container comprising:

means defining a compartment having at least one entrance, sampling head means mounted for communication into said compartment, said sampling head means including a first conduit communicating between a source of pressure and the interior of said compartment and a second conduit communicating between the interior of the sample container and a destination exterior of said compartment for receiving the withdrawn sample, means for selectively closing off said entrance when said container is within said compartment and means establishing a floating pressure seal upon introduction of positive pressure to said compartment when said entrance is closed off, further pressure introduction driving the liquid contents of the sample container through said second conduit to said destination, said means for establishing a floating pressure seal being disposed within the compartment and comprising first and second coaxial collar members arranged in facing relationship and a resilient sealing ring seated between said collar members, at least one of said collar members having a tapered surface facing the other of said collar members and means for moving one of said collar members toward the other upon introduction of pressure thereagainst to expand the sealing member against a surrounding surface whereby to define said seal.

2. Sampling apparatus as claimed in claim 1 in which said means for establishing a floating pressure seal is carried by said sampling head, said sampling head engageable within the open top of said sample container and the pressure-tight seal being established between the sampling head and the interior of said container.

3. The sampling apparatus as claimed in claim 2 in which the height of said compartment is selected to enable reception of said sampling head and container only in engaged condition.

4. Sampling apparatus for withdrawal of liquid samples from an open top sample container comprising:
means defining a compartment having at least one entrance, sampling head means mounted for communication into said compartment, said sampling head means including a first conduit communicating between a source of pressure and the interior of said compartment and a second conduit communicating between the interior of the sample container and a destination exterior of said compartment for receiving the withdrawn sample, means for selectively closing off said entrance when said container is within said compartment and means establishing a floating pressure seal upon introduction of positive pressure to said compartment when said entrance is closed off, further pressure introduction driving the liquid contents of the sample container through said second conduit to said destination, said means for establishing a floating pressure seal being carried by said sampling head, said sampling head being engageable within the open top of said sample container and the pressure-tight seal being established between the sampling head and the interior of said container, said means defining said compartment comprise a pair of opposite parallel side walls and a floor bridging same and joined thereto, channel defining means formed in said opposite side walls and a plate member slidably engageable within said channel defined thereby, said plate carrying said sampling head, and said means for closing off said entrance comprising a depending wall mounted to said plate adapted to cover said entrance when said plate is slidably moved to dispose the sampling head within said compartment.

5. The sampling apparatus as claimed in claim 4 in which said plate has a passageway therein and said sampling head is mounted within said passageway, said sampling head comprising collar means of size and configuration for mounting same within said plate opening, plunger means having a piston at one end and a threaded portion at its opposite end, said plunger means disposed within said collar means for free slidable movement, said piston located on one side of said plate and the threaded portion located on the opposite side of said plate and limit means engaged with said threaded portion for determining the extent of free sliding movement of said plunger means, means defining an adjustable width groove between the piston and collar means and an expansible sealing member disposed within said defined groove, application of positive pressure causing said piston to bear against said sealing member and expand same thereby establishing said pressure seal.

6. The sampling apparatus as claimed in claim 5 in which said open top container is telescopically arranged engaged with said sampling head.

7. The sampling apparatus as claimed in claim 6 in which said piston and said collar means have facing tapered surfaces together defining said adjustable width groove.

8. The sampling apparatus as claimed in claim 4 in which said plate has a second depending wall arranged parallel to said first depending wall and said opening being located between said first and second depending walls, said second depending wall having a free end and flap means coupled to said free end for free pivotal movement relative thereto about an axis taken parallel to said free end.

9. The sampling apparatus as claimed in claim 8 in which said flap means is pivotable to a condition substantially normal relative to said depending wall to enable said flap to support the container engaged with said sampling head within the compartment.

10. The sampling apparatus as claimed in claim 9 in which said entrance includes a rounded edge portion capable of being engaged by said flap.

11. The sampling apparatus as claimed in claim 4 in which said plate has stop means associated therewith for limiting the sliding movement thereof.

12. The sampling apparatus as claimed in claim 4 in which the height of said compartment is selected to just clear the engaged sampling head and container and to maintain such engagement.

13. The sampling apparatus as claimed in claim 5 in which said collar means includes a stationary mounting member secured within the opening in the plate and an annular collar member engaged within said mounting member for sliding movement therethrough, said variable width groove being defined between the ends of said annular collar and the piston.

14. Sampling apparatus for withdrawal of liquid samples from an open top sample container comprising:
means defining a compartment having at least one entrance, sampling head means mounted for communication into said compartment, said sampling head means including a first conduit communicating between a source of pressure and the interior of said compartment and a second conduit communicating between the interior of said compartment for receiving the withdrawn sample, means for selectively closing off said entrance when said container is within said compartment and means establishing a floating pressure seal upon introduction of positive pressure to said compartment when said entrance is closed off, further pressure introduction driving the liquid contents of the sample container through said second conduit to said destination, said last-mentioned means being carried by said sampling head, said sampling head being engageable within the open top of said sample container and the pressuretight seal being established between the sampling head and the interior of said container, and said sampling head comprises an annular collar, a plunger body seated within said collar and freely movable therethrough, stop means on the plunger for limiting said movement, the end of said plunger having an enlarged annular portion provided with a substantially flat outer surface and a tapered undersurface, an expansible O-ring seated upon said tapered undersurface between the enlarged head and said collar, said O-ring being expanded by movement of said piston toward said collar under positive pressure applied thereto.

15. The sampling apparatus as claimed in claim 4 in which said container and said head are frictionally engaged one to the other.

16. The sampling apparatus as claimed in claim 4 in which said container and said sampling head are frictionally coupled one with the other prior to entry thereof into the compartment.

17. The sampling apparatus as claimed in claim 4 in which one wall defining said compartment is movable to place said container and head in coupled condition within said compartment.

18. The sampling apparatus as claimed in claim 17 in which said movable wall carries the sampling head.

19. The sampling apparatus as claimed in claim 17 in which said movable wall carries the sampling head and said means to close off the entrance comprising a wall secured to said movable wall.

20. The sampling apparatus as claimed in claim 17 in which said movable wall comprises a sliding top carrying the sample head through the entrance.

21. Sampling apparatus for withdrawal of liquid samples from an open top sample container comprising:
means defining a bottom-opening compartment having at least one entrance located at the open bottom, sampling head means mounted for communication into said compartment, said sampling head means including a first conduit communication between a source of pressure and the interior of said compartment and a second conduit communicating between the interior of the sample container and a destination exterior of said compartment for receiving the withdrawn sample, means for selectively closing off said entrance when said container is within said compartment comprising a platform and means for selectively raising and lowering said platform and means for positioning the container coaxial with said sample head, means establishing a floating pressure seal upon introduction of positive pressure to said compartment when said entrance is closed off, further pressure introduction driving the liquid contents of the sample container through said second conduit to said destination.

22. The sampling apparatus as claimed in claim 21 in which said means establishing a floating pressure seal is carried by said platform.

23. Sampling apparatus for withdrawal of liquid samples from an open top sample container comprising:
means defining a bottom-opening compartment having at least one entrance located at the open bottom, sampling head means mounted for communication into said compartment, said sampling head means including a first conduit communicating between a source of pressure and the interior of said compartment and a second conduit communicating between the interior of the sample container and and a destination exterior of said compartment for receiving the withdrawn sample, means for selectively closing off said entrance comprising a platform and means for selectively raising and lowering the platform, and means for establishing a floating pressure seal upon introduction of positive pressure to said compartment when said entrance is closed off, further pressure introduction driving the liquid contents of the sample container through said second conduit to said destination.

24. The sampling apparatus as claimed in claim 23 in which said means establishing a floating pressure seal is carried by said platform.

25. The sampling apparatus as claimed in claim 1 in which said entrance is defined transverse the direction of movement of the container.

26. The sampling apparatus as claimed in claim 4 in which the height of said compartment is selected to maintain the engaged relationship of said sampling head and container.

* * * * *